US006969355B2

(12) United States Patent  (10) Patent No.: US 6,969,355 B2
Narimatsu  (45) Date of Patent: Nov. 29, 2005

(54) ARTERIOSTENOSIS DIAGNOSING APPARATUS

(75) Inventor: Kiyoyuki Narimatsu, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 62 days.

(21) Appl. No.: 10/780,574

(22) Filed: Feb. 19, 2004

(65) Prior Publication Data

US 2004/0171940 A1    Sep. 2, 2004

(30) Foreign Application Priority Data

Feb. 28, 2003   (JP)  ............................ 2003-053639

(51) Int. Cl.[7] ............................................... A61B 5/02
(52) U.S. Cl. ........................ 600/481; 600/485; 600/504
(58) Field of Search .............................. 600/300, 301, 600/481–509

(56) References Cited

U.S. PATENT DOCUMENTS

| | | | |
|---|---|---|---|
| 6,355,000 B1 | 3/2002 | Ogura | 600/490 |
| 6,524,257 B2 * | 2/2003 | Ogura | 600/490 |
| 6,669,646 B1 * | 12/2003 | Narimatsu et al. | 600/485 |
| 6,755,792 B2 * | 6/2004 | Masuda et al. | 600/500 |
| 6,843,772 B2 * | 1/2005 | Nunome et al. | 600/481 |

FOREIGN PATENT DOCUMENTS

| | | |
|---|---|---|
| JP | B2 3140007 | 12/2000 |
| JP | A 2002-272688 | 9/2002 |

* cited by examiner

*Primary Examiner*—Robert L. Nasser
*Assistant Examiner*—Patricia Mallari
(74) *Attorney, Agent, or Firm*—Oliff & Berridge, PLC (57) ABSTRACT

An arteriostenosis diagnosing apparatus which measures an ankle blood pressure at an ankle 12 of a patient and a brachium blood pressure at a brachium 14, so that the measured ankle and brachium blood pressure values are used to calculate an ankle and brachium blood pressure index ABI, and additionally measures a first pulse wave propagation velocity PWV1 with respect to the ankle 12 as a first measuring point and the brachium 14 as a second measuring point, and a second pulse wave propagation velocity PWV2 with respect to the patient's heart and the brachium 14. The arteriostenosis diagnosing apparatus includes an arteriostenosis judging device 100 which judges, even if the index ABI may fall in a prescribed normal range or a prescribed alert range and the first velocity PWV1 falls in a prescribed normal range, that there is a possibility that an inferior limb including the ankle 12 at which the ankle blood pressure has been measured, may have arteriostenosis, if the second velocity PWV2 falls in a prescribed abnormal range.

6 Claims, 5 Drawing Sheets

ARTERIOSTENOSIS DIAGNOSING APPARATUS

BACKGROUND OF THE INVENTION

1. Field of the Invention

The present invention relates to an arteriostenosis diagnosing apparatus which diagnoses arteriostenosis of a living subject based on an inferior and superior limb blood pressure index, and pulse wave velocity related information, obtained from the subject.

2. Related Art Statement

Inferior and superior limb blood pressure index is known as an index useful to diagnose arteriostenosis or arterial occlusion resulting from atherosclerosis. This index is expressed as the ratio of superior limb blood pressure to inferior limb blood pressure or the ratio of inferior limb blood pressure to superior limb blood pressure. Generally, systolic blood pressure values are measured to determine this index. In addition, generally, an ankle is used as the inferior limb and a brachium is used as the superior limb, i.e., ankle and brachium blood pressure index ABI is measured as the inferior and superior limb blood pressure index. When a certain portion of an artery has stenosis, a blood pressure in a downstream portion of the artery that is located on a downstream side of the stenotic portion in a direction of flow of blood in the artery is lower than that of an upstream portion of the artery, so that an abnormal inferior and superior limb blood pressure index is obtained and accordingly arteriostenosis can be diagnosed. In many cases, arteriostenosis occurs to an inferior limb of a living being.

Since inferior and superior limb blood pressure index is a simple index, i.e., the ratio of one of inferior and superior limb blood pressure values to the other, it is needed to measure accurate inferior and superior limb blood pressure values so as to obtain the index with reliability. By the way, calcification is a different arteriosclerosis than atherosclerosis. When calcification of a certain portion of an artery progresses, a blood pressure in the calcified portion is higher than that in other portions of the artery. If the calcification further progresses, the blood pressure of the calcified portion becomes still higher, because the calcified portion cannot completely be occluded. Therefore, if calcification of artery progresses in an inferior limb, a normal inferior and superior limb blood pressure index may be obtained even if the inferior limb may have arteriostenosis.

Hence, when a normal inferior and superior limb blood pressure index is obtained, it is needed to judge whether the normal index means that the inferior limb does not have arteriostenosis, or that the inferior limb has not only arteriostenosis but also calcification. To this end, there has been proposed an apparatus which obtains, in addition to inferior and superior limb blood pressure index, pulse wave velocity related information that is related to a velocity at which a pulse wave propagates between two body portions of a living being. This apparatus is disclosed by, e.g., Patent Document 1 (Japanese Patent No. 3,140,007). Since pulse wave velocity related information is useful to evaluate the degree of calcification of artery, whether arteriostenosis is present or not can be judged more reliably based on the pulse wave velocity related information in addition to the inferior and superior limb blood pressure index.

Thus, the purpose of measurement of the pulse wave velocity related information is to determine the degree of calcification of the inferior-limb artery from which the inferior limb blood pressure value used to calculate the inferior and superior limb blood pressure index is measured.

Therefore, recently, it is proposed to obtain pulse wave velocity related information from an interval whose one end is defined by a measurement portion (e.g., an ankle) of an inferior limb where an inferior limb blood pressure value is measured, and which includes an upstream portion of the inferior limb that is located on an upstream side of the measurement portion. This technique is proposed by, e.g., Patent Document 2 (Japanese Patent Publication No. 2002-272688).

However, as the degree of arteriostenosis increases, the pulse wave velocity related information is influenced more and more by the stenosis, and the direction of influence of the stenosis to the information is opposite to that of influence of the calcification. For example, as arteriostenosis progresses, pulse wave velocity decreases; on the other hand, as calcification progresses, the velocity increases. Therefore, in the case where pulse wave velocity related information is obtained from the interval including the upstream portion of the inferior limb, located upstream of the measurement portion where the inferior limb blood pressure is measured, as taught by Patent Document 2, normal pulse wave velocity related information may be obtained depending on respective degrees of arteriostenosis and calcification. Thus, there are some cases where, though arteriostenosis is present, neither pulse wave velocity related information nor inferior and superior limb blood pressure index show abnormal values and accordingly the stenosis cannot be found.

SUMMARY OF THE INVENTION

It is therefore an object of the present invention to provide an arteriostenosis diagnosing apparatus which can more reliably find arteriostenosis of a living subject.

To achieve this object, the Inventor has carried out extensive researches and studies, and found that arteriostenosis of an inferior limb can be found more reliably by determining an inferior and superior limb blood pressure index based on an inferior limb blood pressure obtained at a measuring point on the inferior limb, obtaining first pulse wave velocity related information with respect to a first interval whose one end is defined by the measuring point and which includes an upstream portion of the inferior limb located upstream of the measuring point, obtaining second pulse wave velocity related information from a second interval which does not include any portions of the inferior limb, and judging whether the stenosis is present or not, based on the second pulse wave velocity related information in addition to the blood pressure index and the first velocity related information. More specifically described, calcification of artery is considerably systemic and accordingly, if the second pulse wave velocity related information is abnormal, then there is a high possibility that the first velocity related information may also be abnormal. If, notwithstanding, the first velocity related information is normal, then it can be judged that because arteriostenosis and calcification concurrently progress in the first interval where the first velocity related information is obtained, the first velocity related information appears to be normal and the blood pressure index appears to be not abnormal, i.e., normal or advisory. The present invention has been developed based on this finding.

The above object has been achieved according to the present invention. According to the present invention, there is provided an arteriostenosis diagnosing apparatus, comprising an inferior limb blood pressure measuring device which measures an inferior limb blood pressure at a first measuring point on an inferior limb of a living subject; a superior limb blood pressure measuring device which measures a superior limb blood pressure at a second measuring point on a superior limb of the subject; an inferior and superior limb blood pressure index determining means for determining an inferior and superior limb blood pressure index of the subject, based on the inferior limb blood pressure measured by the inferior limb blood pressure measuring device and the superior limb blood pressure measured by the superior limb blood pressure measuring device; a first pulse wave velocity related information obtaining means for obtaining first pulse wave velocity related information that is related to a first velocity at which a first pulse wave propagates through a first interval whose one end is defined by the first measuring point and which includes an upstream portion of the inferior limb that is located upstream of the first measuring point as seen in a direction of flow of arterial blood in the inferior limb; a second pulse wave velocity related information obtaining means for obtaining second pulse wave velocity related information that is related to a second velocity at which a second pulse wave propagates through a second interval which does not include any portions of the inferior limb; and an arteriostenosis judging means for judging, when the inferior and superior limb blood pressure index does not fall in a prescribed abnormal index range, when the first pulse wave velocity related information falls in a prescribed normal information range, and when the second pulse wave velocity related information falls in a prescribed abnormal information range, that there is a possibility that the inferior limb has arteriostenosis.

There are some cases where, because not only arteriostenosis and but also calcification progress in the inferior limb from which the inferior limb blood pressure used to determine the inferior and superior limb blood pressure index is measured, the blood pressure index does not fall in the prescribed abnormal index range, i.e., falls in a prescribed normal or advisory range, and the first pulse wave velocity related information obtained from the first interval whose one end is defined by the first measuring point where the inferior limb blood pressure is measured and which includes the upstream portion of the inferior limb that is located upstream of the first measuring point falls in the prescribed normal information range. Even in those cases, if the second pulse wave velocity related information obtained from the second interval which does not include any portions of the inferior limb falls in the prescribed abnormal information range, the arteriostenosis judging means judges that there are some possibilities that the inferior limb may have arteriostenosis. Thus, the present apparatus can more reliably find the arteriostenosis of the inferior limb.

Here, preferably, the second pulse wave velocity related information obtaining means obtains the second pulse wave velocity related information that is related to the second velocity at which the second pulse wave propagates through the second interval that is located in an upper half of a body of the subject. If both arteriostenosis and calcification progress in the second interval, as well, where the second pulse wave velocity related information is obtained, and consequently the second velocity related information appears to be normal, it may be difficult to find the arteriostenosis of the inferior limb where the inferior limb blood pressure used to determine the blood pressure index is measured, even if the second velocity related information may be used in addition to the blood pressure index and the first velocity related information. However, since arteriostenosis is less likely to occur to the upper half of the body, the arteriostenosis of the inferior limb where the inferior limb blood pressure is measured, can be found more reliably based on the second velocity related information obtained from the upper half of the body.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
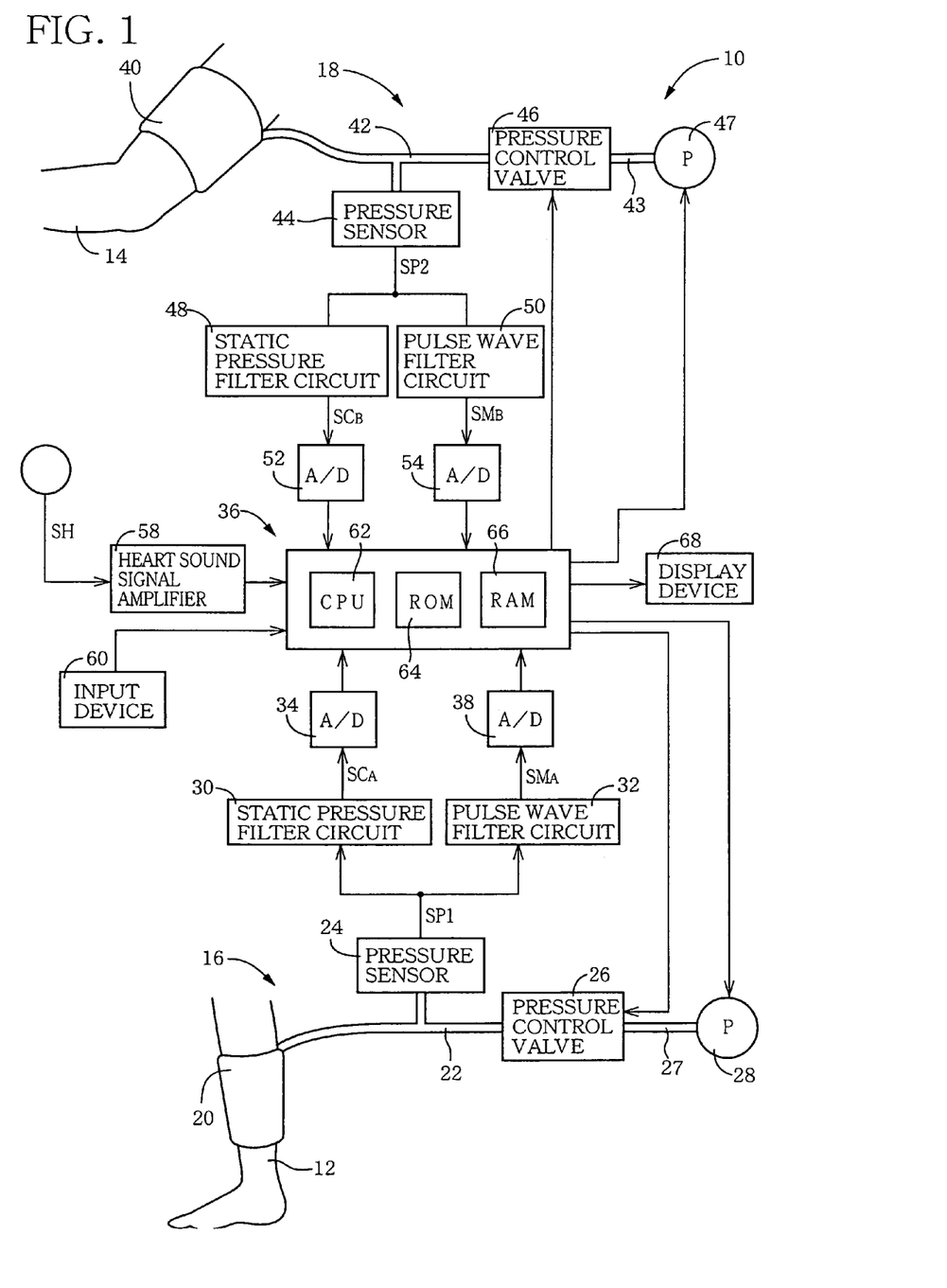
FIG. 1 is a diagrammatic view for explaining a construction of an arteriostenosis diagnosing apparatus to which the present invention is applied.

Hereinafter, there will be described a preferred embodiment of the present invention in detail by reference to the drawings. FIG. 1 is a diagrammatic view for explaining a construction of an arteriostenosis diagnosing apparatus 10. This diagnosing apparatus 10 performs measurements in a state in which a patient as a living subject takes a face-up position or a lateral position, so that a brachium 14 and an ankle 12 of the patient are substantially level with each other.

In FIG. 1, the arteriostenosis diagnosing apparatus 10 includes an ankle blood pressure measuring device 16 which measures a blood pressure of the ankle 12 and functions as an inferior limb blood pressure measuring device; and a brachium blood pressure measuring device 18 which measures a blood pressure of the brachium 14 and functions as a superior limb blood pressure measuring device.

The ankle blood pressure measuring device 16 includes an ankle cuff 20 which includes a belt-like cloth bag and a rubber bag accommodated in the cloth bag and which is adapted to be wound around the ankle 12 of the patient; a pressure sensor 24 and a pressure control valve 26 which are connected to the ankle cuff 20 via a piping 22; and an air pump 28 which is connected to the pressure control valve 26 via a piping 27. The pressure control valve 26 adjusts a pressure of a pressurized air supplied from the air pump 28, and supplies the pressure adjusted air to the ankle cuff 20, or discharges the pressurized air from the ankle cuff 22, so as to control an air pressure in the ankle cuff 20. In the present embodiment, the ankle 12 is an ankle of a left inferior limb (i.e., a left leg) of the patient. However, the ankle cuff 20 may be wound around an ankle of a right inferior limb of the patient.

The pressure sensor 24 detects the air pressure in the ankle cuff 20, and supplies a pressure signal, SP1, representing the detected air pressure, to a static pressure filter circuit 30 and a pulse wave filter circuit 32. The static pressure filter circuit 30 includes a low pass filter which extracts, from the pressure signal SP1, an ankle cuff pressure signal, $SC_A$, representing a static component of the detected air pressure, i.e., a pressing pressure of the ankle cuff 20 (hereinafter, referred to as the ankle cuff pressure, $PC_A$). The filter circuit 30 supplies the ankle cuff pressure signal $SC_A$ to an electronic control device 36 via an A/D (analog to digital converter 34.

The pulse wave filter circuit 32 includes a band pass filter which extracts, from the pressure signal SP1, an ankle pulse wave signal, $SM_A$, representing an ankle pulse wave as an oscillatory component of the detected air pressure that has prescribed frequencies. The filter circuit 32 supplies the ankle pulse wave signal $SM_A$ to the control device 36 via an A/D converter 38. Since the ankle pulse wave signal $SM_A$ represents the ankle pulse wave as the pressure oscillation produced in the ankle cuff 20, the pulse wave filter circuit 32 functions as an ankle pulse wave detecting device.

The brachium blood pressure measuring device 18 includes a brachium cuff 40 which is adapted to be wound around the brachium 14, and additionally includes a pressure sensor 44, a pressure control valve 46, an air pump 47, a static pressure filter circuit 48, and a pulse wave filter circuit 50 which have respective constructions identical with those of the counterparts of the ankle blood pressure measuring device 16. The brachium cuff 40 is connected to the pressure sensor 44 and the pressure control valve 46 via a piping 42; and the pressure control valve 46 is connected to the air pump 47 via a piping 43.

The pressure sensor 44 detects an air pressure in the brachium cuff 40, and supplies a pressure signal, SP2, representing the detected air pressure, to the static pressure filter circuit 48 and the pulse wave filter circuit 50. The static pressure filter circuit 48 extracts, from the pressure signal SP2, a brachium cuff pressure signal, $SC_B$, representing a static component of the detected air pressure, i.e., a pressing pressure of the brachium cuff 40 (hereinafter, referred to as the brachium cuff pressure, $PC_B$). The filter circuit 48 supplies the brachium cuff pressure signal $SC_B$ to the control device 36 via an A/D converter 52. The pulse wave filter circuit 50 extracts, from the pressure signal SP2, a brachium pulse wave signal, $SM_B$, representing a brachium pulse wave as an oscillatory component of the detected air pressure that has prescribed frequencies. The filter circuit 50 supplies the brachium pulse wave signal $SM_B$ to the control device 36 via an A/D converter 54. Since the brachium pulse wave signal $SM_B$ represents the brachium pulse wave as the pressure oscillation produced in the brachium cuff 40, the pulse wave filter circuit 50 functions as a brachium pulse wave detecting device.

A heart sound microphone 56 is attached, with, e.g., an adhesive tape, not shown, to a chest of the patient. The heart sound microphone 56 functions as a heartbeat synchronous signal detecting device which detects heart sounds as a heartbeat synchronous signal. The microphone 56 incorporates a piezoelectric element, not shown, which converts the heart sounds produced from the heart of the patient, into an electric signal, i.e., a heart sound signal SH representing a waveform of the heart sounds. A heart sound signal amplifier 58 incorporates four sorts of filters, not shown, which cooperate with each other to attenuate a low pitch component of the heart sounds that has a great energy, so as to allow clear recording of a high pitch component of the heart sounds. The heart sound signal SH supplied from the heart sound microphone 56 is amplified and filtered by the heart sound signal amplifier 58, and then is supplied to the electronic control device 36 via an A/D converter, not shown.

An input device 60 includes a plurality of numeral keys, not shown, which are manually operable for inputting numerals representing a stature T of the patient, and supplies a stature signal ST representing the patient's stature T inputted through the keys, to the electronic control device 36.

The electronic control device 36 is essentially provided by a microcomputer including a CPU (central processing unit) 62, a ROM (read only memory) 64, a RAM (random access memory) 66, and an I/O (input and output) port, not shown, and the CPU 62 processes signals according to control programs pre-stored in the ROM 64, while utilizing a temporary storage function of the RAM 66. The CPU 62 outputs, from the I/O port, drive signals to the two air pumps 28, 47 and the two pressure control valves 26, 46 so as to control the respective operations thereof and thereby control the respective air pressures of the ankle cuff 20 and the brachium cuff 40. In addition, the CPU 62 processes signals supplied to the control device 36, so as to determine an ankle and brachium blood pressure index ABI, a first pulse wave propagation velocity PWV1, and a second pulse wave propagation velocity PWV2 of the patient, and controls a display device 68 to display the thus determined values ABI, PWV1, PWV2. Moreover, the CPU 62 diagnoses or judges, based on the thus determined values ABI, PWV1, PWV2, whether the left inferior limb of the patient has arteriostensis, and operates the display device 68 to display the result of this diagnosis or judgment.

Figure 2:
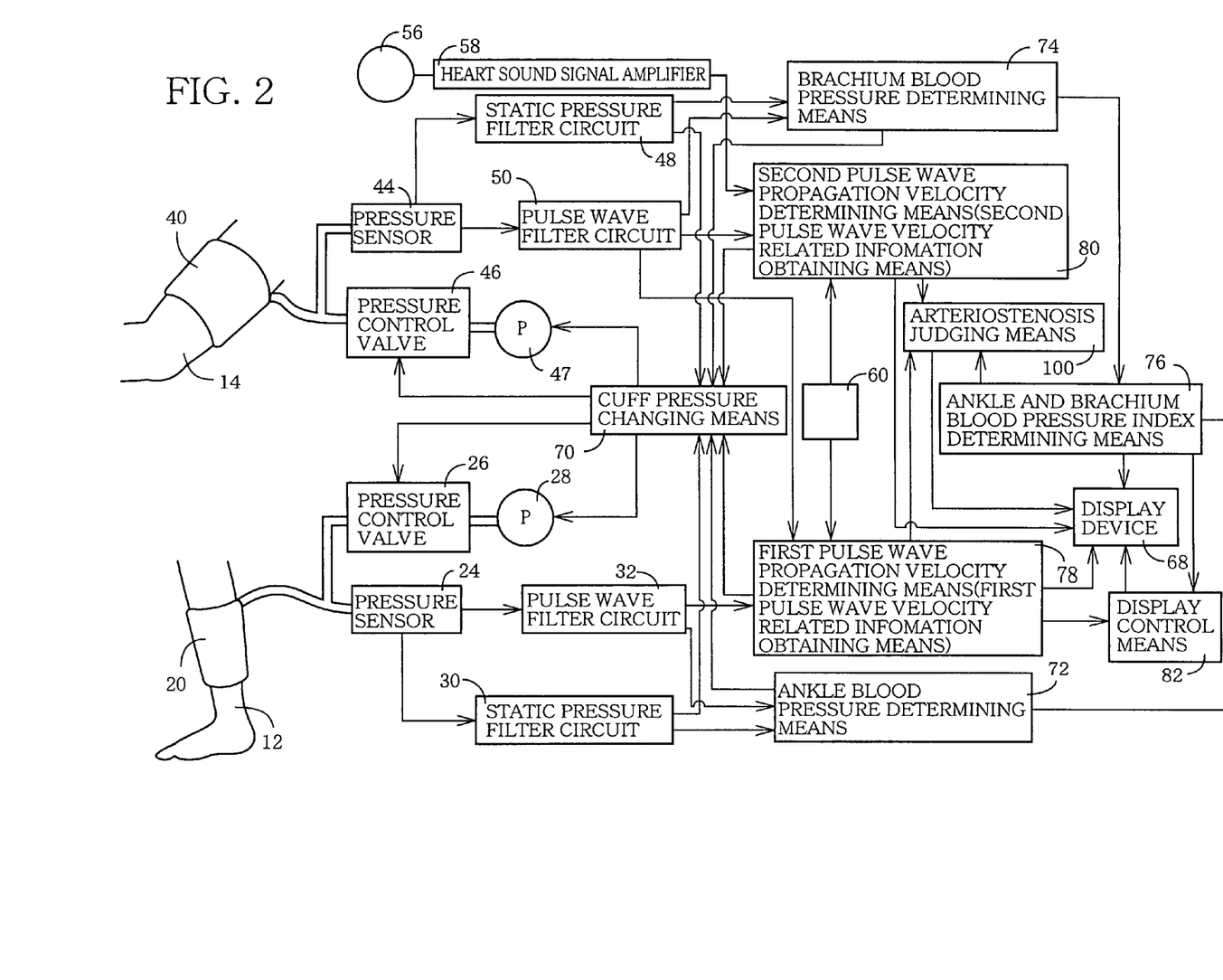
FIG. 2 is a diagrammatic view for explaining essential control functions of an electronic control device of the apparatus of FIG. 1.

FIG. 2 is a diagrammatic view for explaining essential control functions of the electronic control device 36. A cuff pressure changing device or means 70 controls, according to a command signal supplied from an ankle blood pressure determining device or means 72, described later, or a brachium blood pressure determining device or means 72, described later, and based on the ankle and brachium cuff pressure signals $SC_A$, $SC_B$ supplied from the static pressure filter circuits 30, 48, the two air pumps 28, 47, and the two pressure control valves 26, 46 respectively connected to the two pumps 28, 47, so as to change the ankle cuff pressure $PC_A$ and the brachium cuff pressure $PC_B$, as follows: First, the changing means 70 quickly increases the ankle cuff pressure $PC_A$ up to a prescribed first target pressure $PC_{M1}$ (e.g., 240 mmHg) which would be higher than a systolic blood pressure $BP(A)_{SYS}$ of the ankle 12, and then quickly increases the brachium cuff pressure $PC_B$ UP to a prescribed second target pressure $PC_{M2}$ (e.g., 180 mmHg) which would be higher than a systolic blood pressure $BP(B)_{SYS}$ of the brachium 14. Subsequently, the changing means 70 starts slowly decreasing the ankle cuff pressure $PC_A$ and the brachium cuff pressure $PC_B$, slowly at a rate of about 3 mmHg/sec. Finally, after determination of a diastolic blood pressure $BP(A)_{DIA}$ of the ankle 12, the changing means 70 releases the ankle cuff pressure $PC_A$ to atmospheric pressure; and, after determination of a diastolic blood pressure $BP(B)_{DIA}$ of the brachium 14, the changing means 70 releases the brachium cuff pressure $PC_B$ to the atmospheric pressure.

In addition, the cuff pressure changing means 70 controls, according to a command signal supplied from a first pulse wave velocity determining device or means 78, described later, or a second pulse wave velocity determining device or means 80, described later, the two air pumps 28, 47, and the two pressure control valves 26, 46, so as to change the ankle cuff pressure $PC_A$ and the brachium cuff pressure $PC_B$, to a prescribed pulse wave detection pressure.

The ankle blood pressure determining means 72 determines, based on change of respective amplitudes of successive heartbeat synchronous pulses of the ankle pulse wave that is continuously detected when the brachium cuff pressure $PC_A$ is slowly decreased by the cuff pressure changing means 70, blood pressure values of the ankle 12, i.e., an ankle systolic blood pressure $BP(A)_{SYS}$, an ankle mean blood pressure $BP(A)_{MEAN}$, and an ankle diastolic blood pressure $BP(A)_{DIA}$, according to well known oscillometric algorithm. The brachium blood pressure determining means 74 determines, based on change of respective amplitudes of successive heartbeat synchronous pulses of the brachium pulse wave that is continuously detected when the brachium cuff pressure $PC_B$ is slowly decreased by the cuff pressure changing means 70, blood pressure values of the brachium 14, i.e., a brachium systolic blood pressure $BP(B)_{SYS}$, a brachium mean blood pressure $BP(B)_{MEAN}$, and a brachium diastolic blood pressure $BP(B)_{DIA}$, according to the same oscillometric algorithm as used by the ankle blood pressure determining means 72.

An ankle and brachium blood pressure index determining device or means 76, functioning as an inferior and superior limb blood pressure index determining device or means, determines an ankle and brachium blood pressure index ABI of the patient, based on the ankle blood pressure BP(A) determined by the ankle blood pressure determining means 72, and the brachium blood pressure BP(B) that is determined by the brachium blood pressure determining means 74 and corresponds to the sort of ankle blood pressure BP(A) determined. For example, if the systolic ankle blood pressure $BP(A)_{SYS}$ determined by the ankle blood pressure determining means 72 is used, the systolic brachium blood pressure $BP(B)_{SYS}$ determined by the brachium blood pressure determining means 74 is used with the systolic ankle blood pressure $BP(A)_{SYS}$ to determine the ankle and brachium blood pressure index ABI of the patient. The ankle and brachium blood pressure index ABI may be determined by dividing the ankle blood pressure BP(A) by the brachium blood pressure BP(B), or dividing the brachium blood pressure BP(B) by the ankle blood pressure BP(A). The determining means 76 operates the display device 68 to display the thus determined ankle and brachium blood pressure index ABI.

A first pulse wave propagation velocity determining device or means 78 as a first pulse wave propagation velocity related information obtaining device or means reads in the ankle pulse wave signal $SM_A$ and the brachium pulse wave signal $SM_B$ respectively supplied from the pulse wave filter circuit 32 and the pulse wave filter circuit 50, determines respective prescribed periodic points (e.g., respective maximum points or respective rising points) of respective heartbeat synchronous pulses of the ankle pulse wave and the brachium pulse wave that are respectively represented by the ankle pulse wave signal $SM_A$ and the brachium pulse wave signal $SM_B$, and additionally determines a time difference between respective times of detection of the thus determined respective prescribed periodic points of the respective pulses. The respective prescribed periodic points of the respective pulses correspond to each other. For example, if the maximum point of pulse of one of the ankle and brachium pulse waves is determined, then the maximum point of pulse of the other pulse wave is determined. The thus determined time difference is a difference between a time needed for the ankle pulse wave to propagate from the patient's heart to the ankle 12 and a time needed for the brachium pulse wave to propagate from the patient's heart to the brachium 14, and means a pulse wave propagation time DT with respect to the ankle 12 and the brachium 14. This pulse wave propagation time DT is a first pulse wave propagation time DT1, since the left ankle 12 is a first measuring point and this propagation time DT is a time needed for the ankle pulse wave to propagate through a first propagation interval whose one end is defined by the first measuring point and which includes an upstream portion of the left inferior limb of the patient that is located upstream of the left ankle 12. In addition, the pulse wave propagation velocity determining means 78 replaces the following expression (1) defining a relationship between stature T and distance difference L1, with the patient's stature T supplied from the input device 60, and thereby determines a distance difference L1 between a propagation distance from the patient's heart to the ankle 12 and a propagation distance from the patient's heart to the brachium 14, and subsequently replaces the following expression (2) with the thus determined distance difference L1 and the above described first pulse wave propagation time DT1, and thereby determines a first pulse wave propagation velocity PWV1 (cm/sec). Finally, the determining means 78 operates the display device 68 to display the thus determined first pulse wave propagation velocity PWV1:

$$L1=aT+b \qquad \text{Expression (1)}$$

where a, b are experimentally obtained constants, $$PWV1=L1/DT1 \qquad \text{Expression (2)}$$

A second pulse wave propagation velocity determining device or means 80 as a second pulse wave propagation velocity related information obtaining device or means reads in, substantially simultaneously with the reading of the ankle and brachium pulse wave signals $SM_A$, $SM_B$ by the first pulse wave propagation velocity determining means 78, the heart sound signal SH supplied from the heart sound microphone 56 and the brachium pulse wave signal $SM_B$ supplied from the pulse wave filter circuit 50, determines a prescribed periodic point of the heart sound waveform represented by the heart sound signal SH and a prescribed periodic point of the brachium pulse wave represented by the brachium pulse wave signal $SM_B$, and additionally determines a time difference between respective times of detection of the thus determined respective prescribed periodic points of the heart sound waveform and the brachium pulse wave. The respective prescribed periodic points of the heart sound waveform and the brachium pulse wave correspond to each other. For example, if a start point of heart sound II of the heart sound waveform is determined, then a dicrotic notch of the brachium pulse wave that corresponds to the start point is determined. The thus determined time difference is a time needed for the brachium pulse wave to propagate from the patient's heart (i.e., aortic valve) to the brachium 14, and means a pulse wave propagation time DT with respect to the brachium 14. This pulse wave propagation time DT is a second pulse wave propagation time DT2, since this propagation time DT is a time needed for the brachium pulse wave to propagate through a second propagation interval which does not include any portions of the left inferior limb of the patient. In addition, the second pulse wave propagation velocity determining means 80 replaces the following expression (3) defining a relationship between stature T and propagation distance L2, with the patient's stature T supplied from the input device 60, and thereby determines a propagation distance L2 from the patient's heart to the brachium 14, and subsequently replaces the following expression (4) with the thus determined propagation distance L2 and the above described second pulse wave propagation time DT2, and thereby determines a second pulse wave propagation velocity PWV2 (cm/sec). Finally, the determining means 80 operates the display device 68 to display the thus determined second pulse wave propagation velocity PWV2:

$$L2 = cT + d \quad \text{Expression (3)}$$

where c, d are experimentally obtained constants, $$PWV2 = L2/DT2 \quad \text{Expression (4)}$$

Figure 3:
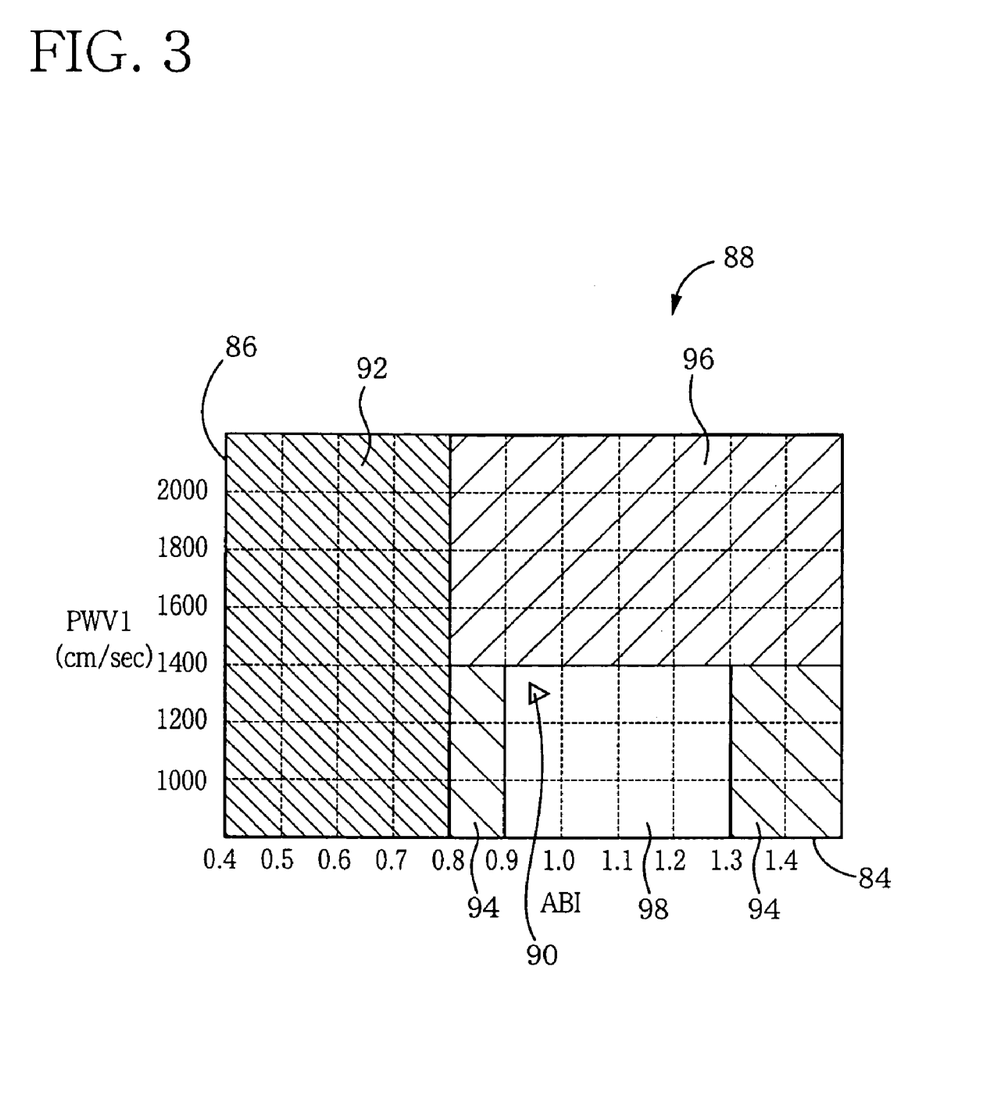
FIG. 3 is a view showing an example of a two dimensional graph that is displayed on a display device under control of a display control means shown in FIG. 2.

A display control device or means 82 controls the display device 68 to display a two-dimensional graph 88, shown in FIG. 3, that is defined by a first axis 84 indicating ankle and brachium blood pressure index ABI and a second axis 86 indicating first pulse wave velocity PWV1, and additionally display a single measured-value symbol 90 representing the ankle and brachium blood pressure index value ABI calculated by the ankle and brachium blood pressure index determining means 76 and the first pulse wave velocity value PWV1 determined by the first pulse wave propagation velocity determining means 78.

The two-dimensional graph 88 shows an abnormal area or range 92, first and second advisory areas or ranges 94, 96 and a normal area. or range 98. If the measured-value symbol 90 falls in the abnormal range 92, then it can be judged that there is a high possibility that the inferior limb including the ankle 12 where the ankle blood pressure values BP(A) were measured may have arteriostenosis and therefore the blood pressure index ABI is abnormal; if the symbol 90 falls in the first or second advisory range 94, 96, then it can be judged that the possibility that the inferior limb including the ankle 12 may have arteriostenosis cannot be denied and therefore it is needed to undergo additional examinations; and if the symbol 90 falls in the normal range 98, then it can be judged that the inferior limb including the ankle 12 does not have arteriostenosis and it is normal. The first advisory range 94 indicates that the first pulse wave velocity PWV1 is normal but the blood pressure index ABI is advisory. Those ranges 92, 94, 96, 98 are determined based on experiments. In the example shown in FIG. 3, when the measured blood pressure index value ABI falls in a range not greater than 0.8, the symbol 90 is displayed in the normal range 92, irrespective of the measured first pulse wave velocity value PWV1; when the measured first velocity value PWV1 falls in a range lower than 1,400 cm/s and the measured blood pressure index value ABI falls in a range from 0.8 to 0.9 or a range greater than 1.3, the symbol 90 is displayed in the first advisory range 94; when the measured first velocity value PWV1 falls in a range not lower than 1,400 cm/s and the measured blood pressure index value ABI falls in a range greater than 0.8, the symbol 90 is displayed in the second advisory range 96; and in other cases, the symbol 90 is displayed in the normal range 98. Since the measured-value symbol 90 is displayed in the two dimensional graph 88 by the display device 68, a medical person such as a doctor or a nurse can judge whether there is any possibility that the patient has arteriostenosis in the inferior limb including the ankle 12, by identifying in which range out of the abnormal range 92, the first advisory range 94, the second advisory range 96, and the normal range 98 the symbol 90 is displayed.

An arteriostenosis judging device or means 100 first judges, based on the ankle and brachium blood pressure index value ABI calculated by the ankle and brachium blood pressure index determining means 76, whether the patient has arteriostenosis in the inferior limb including the ankle 12. More specifically described, when the measured blood pressure index value ABI falls in the prescribed normal range 92, the arteriostenosis judging means 100 judges that the patient has arteriostenosis in the inferior limb including the ankle 12, and operates the display device 68 to display characters and/or symbols indicating this judgment.

When the measured blood pressure index value ABI does not fall in the prescribed normal range 92, then the judging means 100 judges, based on not only the measured blood pressure index value ABI and the measured first velocity value PWV1 but also the measured second velocity value PWV2 determined by the second pulse wave velocity determining means 80, whether the patient has arteriostenosis in the inferior limb including the ankle 12 where the ankle blood pressure values BP(A) were measured. More specifically described, when the measured blood pressure index value ABI falls in the normal range or the advisory range and the measured first velocity value PWV1 falls in the normal range, the judging means 100 judges that there is a high possibility that the patient may have arteriostenosis in the inferior limb including the ankle 12, if the measured second velocity value PWV2 falls in a prescribed abnormal range that indicates arterial calcification. In this case, the judging means 100 operates the display device 68 to display characters and/or symbols indicating this judgment. The reason why, through the measured index value ABI does not fall in the abnormal range 92, the judging means 100 can judge that there is the high possibility that the patient may have arteriostenosis in the inferior limb is as follows: When the measured second velocity value PVV2 indicates arterial calcification, it can be highly expected that the measured first velocity value PWV1 would also indicate arterial calcification. However, in fact, if the measured first velocity value PWV1 is normal, it can be judged that the inferior limb including the measurement interval where the first velocity PWV1 was measured would suffer not only arterial calcification but also arteriostenosis and for this reason the measured first velocity value PWV1 appears to be normal and the measured index value ABI appears to be not abnormal.

Figure 4:
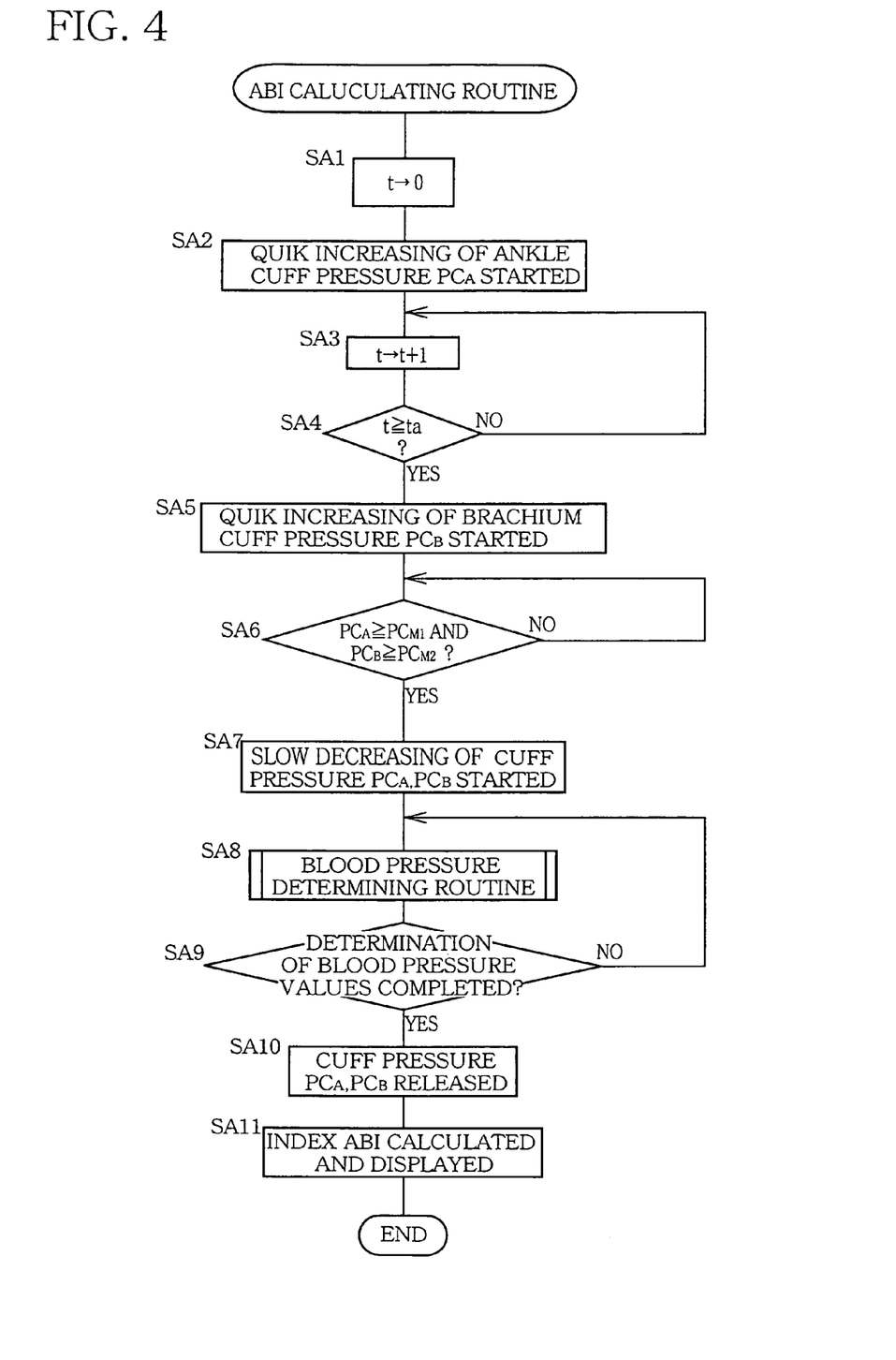
FIG. 4 is a flow chart representing a portion of the essential control functions of the electronic control device, shown in FIG. 2, i.e., an ankle and brachium blood pressure index ABI calculating routine.
Figure 5:
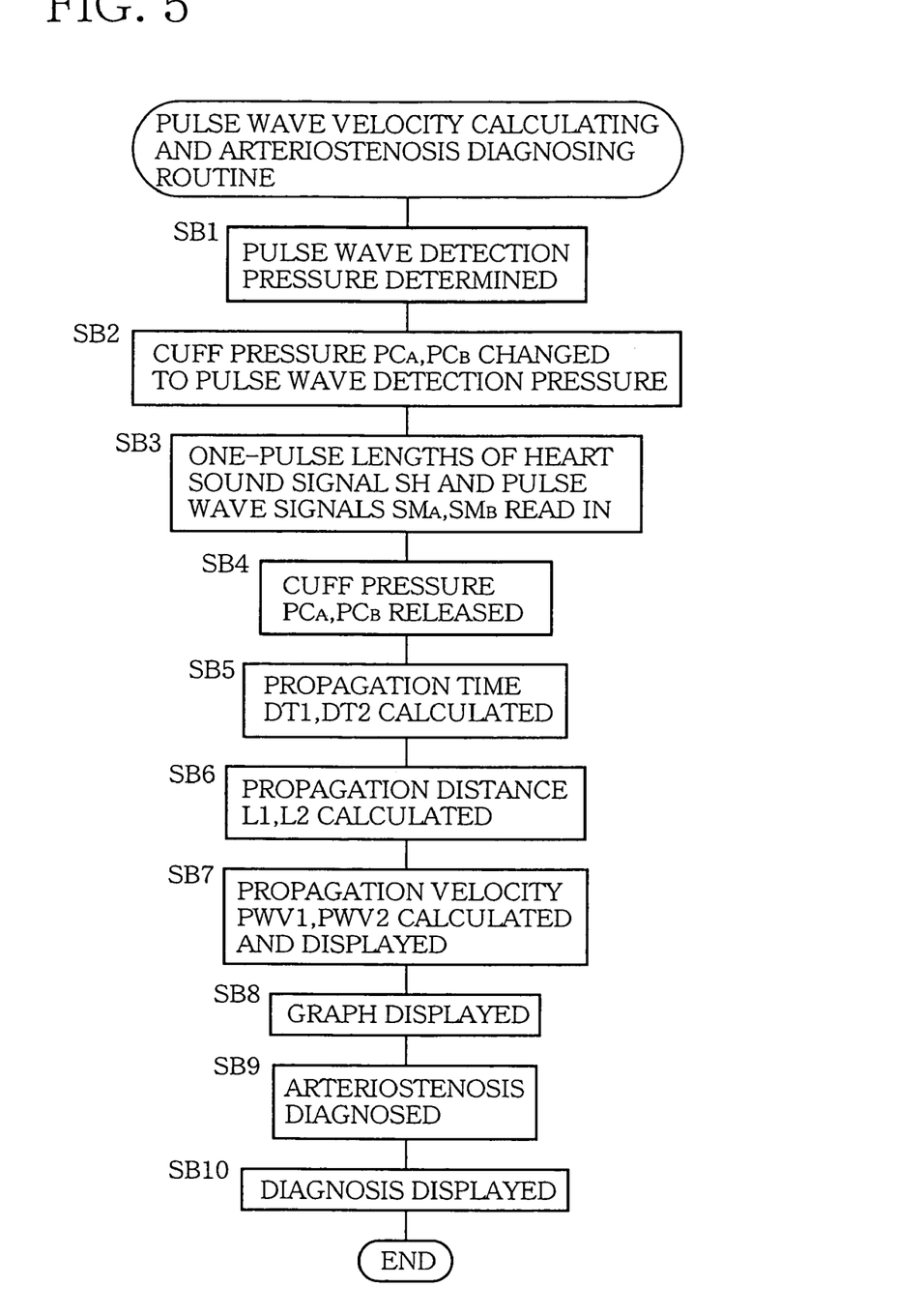
FIG. 5 is another flow chart representing another portion of the essential control functions of the electronic control device, i.e., a pulse wave propagation velocity calculating and arteriostenosis diagnosing routine.

FIGS. 4 and 5 are flow charts representing the control functions of the electronic control device 36, shown in FIG. 2. More specifically explained, FIG. 4 shows an ankle and brachium blood pressure index ABI calculating routine; and FIG. 5 shows a pulse wave propagation velocity calculating and arteriostenosis diagnosing routine that follows the flow chart of FIG. 4. The routines of FIGS. 4 and 5 are started upon operation of a start button, not shown, under the condition that the stature signal ST representing the patient's stature T has already been supplied from the input device 60 to the control device 36.

First, the routine of FIG. 4 is explained. At Step SA1, the control device 36 sets timer, t, to zero (i.e., t=0). Subsequently, at Step SA2, the control device 36 controls the air pump 28 and the pressure control valve 26 so as to start quick increasing of the ankle cuff pressure $PC_A$. Then, at Step SA3, the control device 36 adds one to the timer t (i.e., t=1) and, at Step SA4, the control device 36 judges whether the timer t has reached a prescribed delay time, ta. The delay time ta is so prescribed as to cause the ankle cuff pressure $PC_A$ and the brachium cuff pressure $PC_B$ to reach substantially simultaneously the respective target pressure values $PC_{M1}$, $PC_{M2}$.

If a negative judgment is made at Step SA4, the control device 36 repeats Step SA3 and the following steps to measure a time that has elapsed since the start of increasing of the ankle cuff pressure $PC_A$, while continuing the increasing of the ankle cuff pressure $PC_A$. Meanwhile, if a positive judgment is made at Step SA4, the control of the control device 36 proceeds with Step SA5 to control the air pump 47 and the pressure control valve 46 so as to start quick increasing of the brachium cuff pressure $PC_B$.

Subsequently, the control device 36 judges whether the ankle cuff pressure $PC_A$ has been increased up to the first target pressure $PC_{M1}$, e.g., 240 mmHg and the brachium cuff pressure $PC_B$ has been increased up to the second target pressure $PC_{M2}$, e.g., 180 mmHg. Step SA6 is repeated till a positive judgment is made, while the quick increasing of the ankle and brachium cuff pressure $PC_A$, $PC_B$ is continued. Meanwhile, if a positive judgment is made at Step SA6, the control goes to Step SA7 to stop the air pumps 28, 47 and controls the pressure control valve 26, 46 so as to start slow decreasing of the ankle and brachium cuff pressure $PC_A$, $PC_B$, e.g., at a prescribed rate of 3 mmHg/sec.

Subsequently, at Step SA8 corresponding to the ankle blood pressure determining means 72 and the brachium blood pressure determining means 74, the control device 36 carries out a blood pressure determining routine. More specifically described, the control device 36 stores the ankle cuff pressure signal $SC_A$ and the ankle pulse wave signal $SM_A$ respectively supplied from the static pressure filter circuit 30 and the pulse wave filter circuit 32, determines respective values of the ankle cuff pressure $PC_A$ represented by the ankle cuff pressure signal $SC_A$ and respective amplitudes of successive heartbeat synchronous pulses of the ankle pulse wave represented by the ankle pulse wave signal $SM_A$, and determines, based on the thus determined respective values of the ankle cuff pressure $PC_A$ and the thus determined respective amplitudes of successive heartbeat synchronous pulses of the ankle pulse wave, an ankle systolic blood pressure $BP(A)_{SYS}$, an ankle mean blood pressure $BP(A)_{MEAN}$, and an ankle diastolic blood pressure $BP(A)_{DIA}$ of the patient, according to a well-known oscillometric blood pressure determining algorithm. Likewise, the control device 36 stores the brachium cuff pressure signal $SC_B$ supplied from the static pressure filter circuit 48, and the brachium pulse wave signal $SM_B$ supplied from the pulse wave filter circuit 50, determines respective values of the brachium cuff pressure $PC_B$ represented by the brachium cuff pressure signal $SC_B$ and respective amplitudes of successive heartbeat synchronous pulses of the brachium pulse wave represented by the brachium pulse wave signal $SM_B$, and determines, based on the thus determined respective values of the brachium cuff pressure $PC_B$ and the thus determined respective amplitudes of successive heartbeat synchronous pulses of the brachium pulse wave, a brachium systolic blood pressure $BP(B)_{SYS}$, a brachium mean blood pressure $BP(B)_{MEAN}$, and a brachium diastolic blood pressure $BP(B)_{DIA}$ of the patient, according to the oscillometric blood pressure determining algorithm.

Then, at Step SA9, the control device 36 judges whether the determination of ankle and brachium blood pressure values BP(A), BP(B) at Step SA8 has been completed. Since the cuff pressure $PC_A$, $PC_B$ are slowly decreased, the diastolic blood pressure values $BP(A)_{DIA}$, $BP(B)_{DIA}$ are determined last. Therefore, at Step SA9, the control device judges whether the diastolic blood pressure values $BP(A)_{DIA}$, $BP(B)_{DIA}$ have been determined. If a negative judgment is made at Step SA9, the control device 36 repeats Step SA8 and the following steps. Meanwhile, if a positive judgment is made at Step SA9, the control goes to Step SA10 so as to control the pressure control valves 26, 46 to release the ankle and brachium cuff pressure $PC_A$, $PC_B$ to atmospheric pressure.

Subsequently, at Step SA7, the control device 36 carries out Step SA11 corresponding the ankle and brachium blood pressure index determining means 76. At Step SA11, the control device 36 divides the ankle systolic blood pressure $BP(A)_{SYS}$ determined at Step SA8, by the brachium systolic blood pressure $BP(B)_{SYS}$ also determined at Step SA8, and operates the display device 68 to display the thus determined index value ABI. Following Step SA11, the control proceeds with the routine shown in FIG. 5.

Next, the routine of FIG. 5 will be described. First, at Step SB1, the control device 36 determines, for the ankle 12, an ankle pulse wave detection pressure by subtracting a prescribed pressure, α, from the ankle diastolic blood pressure $BP(A)_{DIA}$ determined at Step SA8 of FIG. 4, and additionally determines, for the brachium 14, a brachium pulse wave detection pressure by subtracting the prescribed pressure a from the brachium diastolic blood pressure $BP(B)_{DIA}$ also determined at Step SA8. Subsequently, at Step SB2, the control device 36 re-starts the air pumps 28, 47 and controls the pressure control valves 26, 46 so as to change and kept the ankle and brachium cuff pressure $PC_A$, $PC_B$ to and at the ankle and brachium pulse wave detection pressures determined at Step SB1.

Then, at Step SB3, the control device 36 reads in respective one-pulse lengths of the heart sound signal SH supplied from the heart sound microphone 56 via the signal amplifier 58, the ankle pulse wave signal $SM_A$ supplied from the pulse wave filter circuit 32, and the brachium pulse wave signal $SM_B$ supplied from the pulse wave filter circuit 50. Subsequently, at Step SB4, the control device 36 stops the air pumps 28, 47 and controls the pressure control valves 26, 46 so as to release the ankle and brachium cuff pressure $PC_A$, $PC_B$ to the atmospheric pressure. In the flow charts shown in FIGS. 4 and 5, Steps SA1 to SA7, SA10, SB1, SB2, and SB4 correspond to the cuff pressure changing means 70.

Then, the control goes to Steps SB5, SB6, and SB7 corresponding to the first and second pulse wave velocity determining means 78, 80. First, at Step SB5, the control device 36 determines a start point of a heart sound II of the heart sound waveform represented by the heart sound signal SH read in at Step SB3, respective rising points of the ankle and brahcium pulse waves represented by the ankle and brachium pulse wave signals $SM_A$, $SM_B$ also read in at Step SB3, and a dicrotic notch of the brachium pulse wave. In addition, the control device 36 calculates, as a first pulse wave propagation time DT1, a time difference between a time of detection of the rising point of the ankle pulse wave and a time of detection of the rising point of the brachium pulse wave, and additionally calculates, as a second pulse wave propagation time DT2, a time difference between a time of detection of the start point of the heart sound II and a time of detection of the dicrotic notch of the brachium pulse wave that corresponds to the start point of the heart sound II.

Subsequently, at Step SB6, the control device 36 substitutes the above-indicated expressions (1) and (3) with the patient's stature T represented by the stature signal ST supplied from the input device 60, so as to determine a distance difference L1 between a propagation distance between the patient's heart and the ankle 12 and a propagation distance L2 between the patient's heart and the brachium 14, and the propagation distance L2 between the patient's heart and the brachium 14, respectively. Then, at Step SB7, the control device 36 substitutes the above-indicated expression (2) with the first pulse wave propagation time DT1 determined at Step SB5 and the distance difference L1 determined at Step SB6, so as to calculate a first pulse wave propagation velocity PWV1 (cm/sec), and additionally substitutes the above-indicated expression (4)

with the second pulse wave propagation time DT2 determined at Step SB5 and the propagation distance L2 determined at Step SB6, so as to calculate a second pulse wave propagation velocity PWV2 (cm/sec). Then, the control device 36 operates the display device 68 to display the thus calculated first and second pulse wave propagation velocity values PWV1, PWV2.

Subsequently, at Step SB8 corresponding to the display control means 82, the control device 36 controls the display device 68 to display the two dimensional graph 88, as shown in FIG. 3, and additionally display, in the graph 88, the measured-value symbol 90 representing the ankle and brachium blood pressure index ABI calculated at Step SA11 and the first pulse wave propagation velocity PWV1 calculated at Step SB7.

Then, the control goes to Steps SB9 and SB10 corresponding to the arteriostenosis judging means 100. At Step SB9, first, the control device 36 judges, when the ankle and brachium blood pressure index value ABI, calculated at Step SA11, falls in the normal range 92, that the patient has arteriostenosis in the inferior limb including the ankle 12. Second, even if the blood pressure index value ABI may not fall in the abnormal range 92, but, if the first pulse wave velocity PWV1 calculated at Step SB7 falls in the normal range and if the second velocity value PWV2 also calculated at Step SB7 falls in the abnormal range, the control device 36 judges that there is a high possibility that the patient may have arteriostenosis in the inferior limb including the ankle 12.

Finally, at Step SB10, the control device 36 operates the display device 68 to display characters and/or symbols indicating the judgment made at Step SB9.

In the illustrated embodiment, in the case where the inferior limb including the ankle 12 where the ankle blood pressure value BP(A) is measured, suffers not only arteriostenosis but also calcification and accordingly the ankle and brachium blood pressure index ABI falls in the normal or advisory range and the first pulse wave velocity PWV1 measured with respect to the ankle 12 and the brachium 14 falls in the normal range, the arteriostenosis judging means 100 (Steps SB9 and SB10) judges that there is a high possibility that the patient may have arteriostenosis in the inferior limb including the ankle 12, if the second pulse wave velocity PWV2 measured with respect to the measurement interval between the patient's heart and the brachium 14 that does not include any portions of the inferior limb. Thus, the present apparatus 10 can more reliably find the arteriostenosis of the inferior limb of the subject.

In the illustrated embodiment, in particular, the second pulse wave velocity PWV2 is measured with respect to the measurement interval between the patient's heart and the brachium 14, i.e., a measurement interval located in an upper half of the patient's body. Since the upper half body is less likely to suffer arteriostenosis than the lower half body, the present apparatus 10 can still more reliably find the arteriostenosis of the inferior limb including the ankle 12.

While the present invention has been described in its embodiment by reference to the drawings, it is to be understood that the invention may otherwise be embodied.

For example, in the illustrated embodiment, the first pulse wave velocity PWV1 is measured with respect to the ankle 12 as one of the two measuring points and the brachium 14 as the other measuring point. However, the brachium 14 as the other measuring point may be replaced with different portions of the subject, such as the heart, a wrist, or a cerebral portion.

In addition, in the illustrated embodiment, the second pulse wave velocity PWV2 is measured with respect to the measurement interval between the patient's heart and the brachium 14. However, the measurement interval between the patient's heart and the brachium 14 may be replaced with different measurement intervals located in the upper half of the patient's body, such as an interval between the heart and a cerebral portion, an interval between the brachium 14 and a wrist. Otherwise, the measurement interval between the patient's heart and the brachium 14 may be replaced with different measurement intervals located in the lower half of the patient's body, such as an interval between the heart and an inferior limb different from the inferior limb including the ankle 12 where the ankle blood pressure BP(A) is measured.

It is to be understood that the present invention may be embodied with other changes, improvements and modifications that may occur to a person skilled in the art without departing from the spirit and scope of the invention defined in the appended claims.

What is claimed is:

1. An arteriostenosis diagnosing apparatus, comprising:
   an inferior limb blood pressure measuring device which measures an inferior limb blood pressure at a first measuring point on an inferior limb of a living subject;
   a superior limb blood pressure measuring device which measures a superior limb blood pressure at a second measuring point on a superior limb of the subject;
   an inferior and superior limb blood pressure index determining means for determining an inferior and superior limb blood pressure index of the subject, based on the inferior limb blood pressure measured by the inferior limb blood pressure measuring device and the superior limb blood pressure measured by the superior limb blood pressure measuring device;
   a first pulse wave velocity related information obtaining means for obtaining first pulse wave velocity related information that is related to a first velocity at which a first pulse wave propagates through a first interval whose one end is defined by the first measuring point and which includes an upstream portion of the inferior limb that is located upstream of the first measuring point as seen in a direction of flow of arterial blood in the inferior limb;
   a second pulse wave velocity related information obtaining means for obtaining second pulse wave velocity related information that is related to a second velocity at which a second pulse wave propagates through a second interval which does not include any portions of the inferior limb; and
   an arteriostenosis judging means for judging, when the inferior and superior limb blood pressure index does not fall in a prescribed abnormal index range, when the first pulse wave velocity related information falls in a prescribed normal information range, and when the second pulse wave velocity related information falls in a prescribed abnormal information range, that there is a possibility that the inferior limb has arteriostenosis.

2. The apparatus according to claim 1, wherein the second pulse wave velocity related information obtaining means obtains the second pulse wave velocity related information that is related to the second velocity at which the second pulse wave propagates through the second interval that is located in an upper half of a body of the subject.

3. The apparatus according to claim 1, wherein the inferior limb blood pressure measuring device comprises an inferior limb cuff which is adapted to be worn on the first measuring point of the inferior limb of the subject, and the superior limb blood pressure measuring device comprises a superior limb cuff which is adapted to be worn on the second measuring point of the superior limb of the subject, wherein the inferior and superior limb blood pressure index determining means determines the inferior and superior limb blood pressure index of the subject, by dividing one of the inferior limb blood pressure and the superior limb blood pressure by the other of the inferior limb blood pressure and the superior limb blood pressure, wherein the first pulse wave velocity related information obtaining means comprises a first pulse wave velocity determining means for determining the first pulse wave velocity at which the first pulse wave propagates through the first interval whose length is equal to a difference between a first distance between a heart of the subject and the first measuring point and a second distance between the heart of the subject and the second measuring point, and the second pulse wave velocity related information obtaining means comprises a second pulse wave velocity determining means for determining the second pulse wave velocity at which the second pulse wave propagates through the second interval whose length is equal to the second distance between the heart of the subject and the second measuring point, and wherein the arteriostenosis judging means judges, when the inferior and superior limb blood pressure index falls in a prescribed normal index range or a prescribed advisory index range other than the abnormal index range, when the first pulse wave velocity falls in a prescribed normal first velocity range, and when the second pulse wave velocity falls in a prescribed abnormal second velocity range, that there is the possibility that the inferior limb has the arteriostenosis.

4. The apparatus according to claim 3, further comprising:
a display device which displays a screen image; and
a display control means for controlling the display device to display, as the screen image, a two-dimensional graph that is defined by a first axis indicating inferior and superior limb blood pressure index, and a second axis indicating first pulse wave velocity, and additionally display a determined-value symbol representing the inferior and superior limb blood pressure index determined by the inferior and superior limb blood pressure index determining means and the first pulse wave velocity determined by the first pulse wave velocity determining means.

5. The apparatus according to claim 3, wherein the second pulse wave velocity determining means comprises:
a heart sound microphone which is adapted to be worn on the heart of the subject and detects a heart sound produced by the heart;
the superior limb cuff which detects the second pulse wave at the second measuring point;
means for determining, as a propagation time, a time difference between respective prescribed periodic points of the heart sound detected by the heart sound microphone and the second pulse wave detected by the superior limb cuff, and
means for determining the second pulse wave velocity by dividing the length of the second interval by the determined propagation time.

6. An arteriostenosis diagnosing apparatus, comprising:
an inferior limb blood pressure measuring device which measures an inferior limb blood pressure at a first measuring point on an inferior limb of a living subject;
a superior limb blood pressure measuring device which measures a superior limb blood pressure at a second measuring point on a superior limb of the subject;
an inferior and superior limb blood pressure index determining device which determines an inferior and superior limb blood pressure index of the subject, based on the inferior limb blood pressure measured by the inferior limb blood pressure measuring device and the superior limb blood pressure measured by the superior limb blood pressure measuring device;
a first pulse wave velocity related information obtaining device which obtains first pulse wave velocity related information that is related to a first velocity at which a first pulse wave propagates through a first interval whose one end is defined by the first measuring point and which includes an upstream portion of the inferior limb that is located upstream of the first measuring point as seen in a direction of flow of arterial blood in the inferior limb;
a second pulse wave velocity related information obtaining device which obtains second pulse wave velocity related information that is related to a second velocity at which a second pulse wave propagates through a second interval which does not include any portions of the inferior limb; and
an arteriostenosis judging device which judges, when the inferior and superior limb blood pressure index does not fall in a prescribed abnormal index range, when the first pulse wave velocity related information falls in a prescribed normal information range, and when the second pulse wave velocity related information falls in a prescribed abnormal information range, that there is a possibility that the inferior limb has arteriostenosis.

* * * * *